Figure 1:
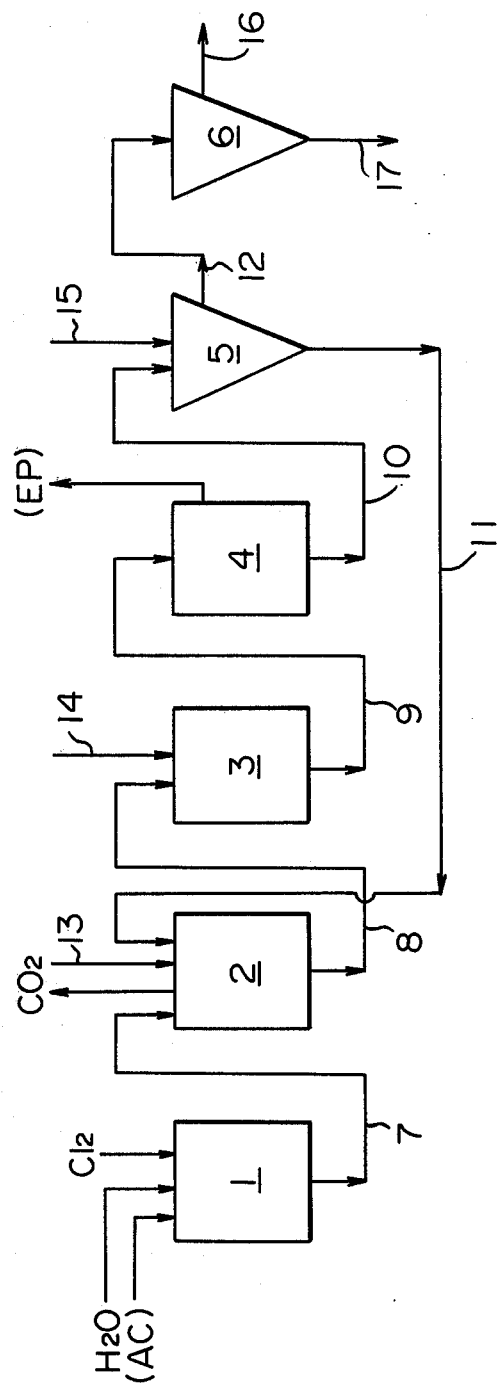

United States Patent [19]

Kawabe et al.

[11] 4,113,746

[45] Sep. 12, 1978

[54] PROCESS FOR CONTINUOUS PRODUCTION OF EPICHLOROHYDRIN

[75] Inventors: Takamasa Kawabe; Masaaki Kadoma; Kazuyoshi Murakami; Hatuhide Itoh, all of Kurashiki, Japan

[73] Assignee: Osaka Soda Co., Ltd., Osaka, Japan

[21] Appl. No.: 748,473

[22] Filed: Dec. 8, 1976

[30] Foreign Application Priority Data

Dec. 9, 1975 [JP] Japan ............................. 50-147062

[51] Int. Cl.$^2$ ............................................ C07D 301/26
[52] U.S. Cl. .............................................. 260/348.22
[58] Field of Search ........................ 260/348.6, 348.22

[56] References Cited

U.S. PATENT DOCUMENTS 2,177,419  10/1939  Engs et al. ........................ 260/348.6

FOREIGN PATENT DOCUMENTS 47,363  1972  Japan.
5,203  3/1969  Japan.

OTHER PUBLICATIONS

Chemical Abstracts, vol. 83 (1975), abstracting Hine, Fumio, Soda to Enso (1975), vol. 26(3), pp. 69–76 (Japan).

Primary Examiner—Norma S. Milestone
Attorney, Agent, or Firm—Sherman & Shalloway

[57] ABSTRACT

A process for continuously producing epichlorohydrin which comprises reacting chlorine and allyl chloride in an aqueous medium, neutralizing and saponifying the resulting hydrochloric acid-acidified solution containing glycerol dichlorohydrin with an alkali to form a solution containing epichlorohydrin, and separating epichlorohydrin from the resulting solution; wherein (1) the neutralization and saponification are performed in separately provided neutralization and saponification zones, (2) a slurry containing mainly calcium carbonate and calcium hydroxide is separated from the residual slurry left after the separation of epichlorohydrin, and (3) the neutralization and saponification reactions are carried out while recycling the separated slurry containing calcium carbonate and calcium hydroxide into the neutralization zone.

4 Claims, 1 Drawing Figure

PROCESS FOR CONTINUOUS PRODUCTION OF EPICHLOROHYDRIN

This invention relates to a process for continuously producing epichlorohydrin, and more specifically, to a process for continuously producing epichlorohydrin in high yields with commercial advantage by recycling a part of the residual slurry left after separation of epichlorohydrin whereby the difficulty of disposal of the residual slurry is overcome, the amount of alkali required for neutralization is reduced, and side-reactions are advantageously avoided.

A process for producing epichlorohydrin has been known which comprises reacting chlorine and allyl chloride in an aqueous medium, neutralizing and saponifying the resulting hydrochloric acid-acidified solution containing glycerol dichlorohydrin with an excess of alkali to form a solution containing epichlorohydrin, and separating epichlorohydrin from the solution. In this known process, the hydrochloric acid-acidified solution containing glycerol dichlorohydrin is saponified with an excess of alkali, usually calcium hydroxide. The alkali is consumed not only for the saponification reaction, but also for the neutralization of hydrochloric acid formed as a by-product of the reaction between chlorine and allyl chloride. It is well known on the other hand that in order to obtain epichlorohydrin in high yields, the alkali must be used in excess. From the standpoint of pollution control, the residual slurry left after the separation of epichlorohydrin cannot be directly discarded, but must be neutralized in advance by using complicated and disadvantageous operations and devices. When slaked lime is used either alone or together with an alkali hydroxide, the slaked lime remains in the residual slurry, and its treatment becomes more complicated.

In an attempt to reduce the amount of expensive calcium hydroxide used for neutralization, a suggestion was made in Japanese Patent Publication No. 47363/72 in which a low-cost insoluble carbonate such as calcium carbonate is first added to the hydrochloric acid-acidified solution containing glycerol dichlorohydrin as a product obtained by the neutralization and saponification with alkali, thereby to neutralize the hydrochloric acid, and then slaked lime is added to perform the saponification reaction. This Japanese patent discloses that the cost of production can be reduced, and epichlorohydrin can be obtained in an increased yield while reducing the amounts of by-products formed. The patent, however, is quite silent on the separation of a slurry containing mainly $CaCO_3$ and $Ca(OH)_2$ from the residue left after the separation of epichlorohydrin, and its recycling and reuse in the neutralization reaction.

The present inventors made extensive investigations in order to provide an improved process for continuously producing epichlorohydrin. These investigations finally led to the present invention that provides a process for producing epichlorohydrin continuously which comprises reacting chlorine and allyl chloride in an aqueous medium, neutralizing and saponifying the resulting hydrochloric acid-acidified solution containing glycerol dichlorohydrin with an alkali to form a solution containing epichlorohydrin as a product, and separating epichlorohydrin from the solution, wherein (1) the neutralization and saponification are performed in separately provided neutralization and saponification zones, (2) a slurry containing mainly $CaCO_3$ and $Ca(OH)_2$ is separated from the residual slurry left after the separation of epichlorohydrin, and (3) the neutralization and saponification are performed while the separated slurry containing $CaCO_3$ and $Ca(OH)_2$ is being recycled to the neutralization zone.

Thus, the residual slurry which is left after separation of epichlorohydrin and of which disposal has previously caused many troubles from the standpoint of pollution control can be advantageously reused in the reaction, and the residual slurry can be very easily treated. In addition, side-reactions that may be induced by the reuse of the residual slurry can be advantageously avoided, and epichlorohydrin produced in high yields at lower costs.

It has been found that in separating the slurry containing mainly calcium carbonate and calcium hydroxide from the residual slurry, the rate of sedimentation of the calcium component can be increased over that of the magnesium component by sedimenting the residual slurry in the presence of calcium carbonate added, whereby a slurry containing mainly calcium carbonate and calcium hydroxide can be conveniently sedimented and separated while leaving a component containing mainly magnesium hydroxide in the slurry. It has also been found that the use of the slurry so separated can advantageously obviate the formation of by-products such as chloro-propionaldehyde and glycerol which is induced during the saponification reaction by magnesium salts which are necessarily deposited when using the residual slurry directly without separation. Furthermore, the remainder of the slurry can be very simply treated.

Thus, according to the process of this invention pollution can be avoided by skillfully utilizing the residual slurry left after the separation of epichlorohydrin of which disposal has previously caused many troubles and disadvantages, and the occurrence of side reactions can be advantageously inhibited. Furthermore, epichlorohydrin can be produced selectively in high yields by using alkali in an amount required substantially stoichiometrically for the saponification of glycerol dichlorohydrin. Since the reaction proceeds smoothly by using a stoichiometrical amount of alkali, the remainder of the residual slurry mainly contains magnesium and can be easily discarded or effectively utilized. It can be disposed of merely by separating magnesium hydroxide by sedimentation.

Accordingly, it is an object of this invention to provide an improved process for continuously producing epichlorohydrin in a high yield at low cost and with commercial advantages.

Other objects and advantages of the invention will become more apparent from the following description.

In order to facilitate the understanding of the invention, one embodiment of the process of this invention will be described below by reference to the accompanying drawing (FIG. 1) which is a flowsheet showing one typical example of the process of this invention.

Referring to FIG. 1, the reference numeral 1 represents a reaction zone in which chlorine is reacted with allyl chloride (AC) in an aqueous medium to form a solution which contains the resulting glycerol dichlorohydrin (DH) and which has been rendered acidic by hydrochloric acid formed in the reaction. A neutralization zone for neutralizing the DH-containing solution from the reaction zone 1 is shown at 2, and a saponification zone for reacting the neutralized reaction product liquid from the neutralization zone 2 with calcium hydroxide or an alkali hydroxide containing at least 50% by weight of calcium hydroxide thereby to form epichlorohydrin (EP) is designated at 3. Epichlorohydrin is separated in a zone 4 from the epichlorohydrin-containing liquid from the saponification zone 3, and a slurry containing mainly calcium carbonate and calcium hydroxide is separated in a sedimentation zone 5 from the residual slurry that has left the separating zone 4. The slurry containing mainly magnesium hydroxide which has left the sedimentation zone 5 is then subjected to a sedimentation treatment in a sedimentation zone 6 thereby to sediment and separate the magnesium hydroxide component.

Chlorine gas and AC in a substantially equimolar ratio, for example, 1: about 0.90 – about 0.95 (molar ratio) and an aqueous medium usually water are introduced into the reaction zone 1 to form a hydrochloric acid-acidified solution containing about 2 to 5% by weight of DH. The amount of the by-product hydrochloric acid is substantially equimolar to that of DH. This reaction is schematically shown as follows:

$$CH_2Cl\text{-}CH=CH_2 + Cl_2 + H_2O \rightarrow CH_2Cl\text{-}CHCl\text{-}CH_2OH + HCl$$

The reaction can be performed at a temperature of 40° to 60° C under atmospheric pressure with a residence time of about 60 to about 120 minutes.

The DH-containing hydrochloric acid-acidified reaction product is continuously fed into the neutralization zone 2 through a line 7 to neutralize the by-product hydrochloric acid. The slurry mainly containing calcium carbonate and calcium hydroxide separated in the sedimentation zone 5 is fed through a line 11 into the neutralization zone. When the amount of a hydrochloric acid-neutralizing component consisting mainly of calcium carbonate and calcium hydroxide in the recycle slurry is sufficient for neutralizing hydrochloric acid, it is not necessary to supply it further. However, when it is insufficient for neutralization, additional amounts of calcium carbonate and/or calcium hydroxide can be fed through a line 13. Carbon dioxide formed as a by-product as a result of the neutralization reaction of hydrochloric acid and calcium carbonate can be recovered if desired through a carbon dioxide withdrawal pipe. A flow of the product neutralized in the neutralizing zone 2 is conducted to the saponification zone 3 through a line 8, and subjected to a saponification reaction. Calcium hydroxide may be fed into the saponification zone though a line 14. Usually, calcium hydroxide can be added in the form of 10-20% by weight lime milk. The conversion of DH to EP in the saponification zone can be performed by the reaction schematically shown below.

$2CH_2Cl \cdot CHCl \cdot CH_2OH + Ca(OH)_2$
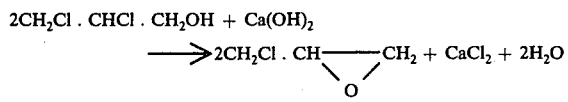
$+ CaCl_2 + 2H_2O$

The reaction can be carried out at 80° to 100° C under atmospheric pressure with a residence time of about 5 to about 10 minutes. The amount of the alkali in the saponification reaction system is about 1.05 to about 1.2 times the stoichiometrical amount.

The EP-containing solution so formed is introduced into the EP-separating zone 4 through a line 9. EP is recovered as an azeotrope with water by distillation in the zone 4, and can be purified in a purifying step (not shown). The remainder of the residual slurry left after separation of EP in the zone 4 is introduced into the sedimentation zone 5 for separating a slurry containing mainly calcium carbonate and calcium hydroxide from the residual slurry. The calcium hydroxide or both calcium hydroxide and calcium carbonate in the residual slurry have a higher rate of sedimentation in the zone 5 than that of magnesium hydroxide derived from MgO impurity in the alkali used for neutralization and saponification, that is, calcium hydroxide or an alkali hydroxide containing at least 50% by weight of calcium hydroxide, and sediments earlier to the bottom of the sedimentation zone 5. Thus, the deposit on the bottom, which is a slurry containing mainly calcium carbonate and calcium hydroxide, is separated, and recycled to the neutralization zone 2 through line 11 to neutralize hydrochloric acid in the DH-containing hydrochoric acid - acidified solution.

When calcium carbonate added is present in the system during the above sedimentation, the difference in sedimentation speed between the mixture consisting mainly of calcium carbonate and calcium hydroxide and the magnesium hydroxide component increases conveniently. Hence, in a preferred embodiment of the process of this invention, it is especially advantageous to perform the sedimentation operation in the presence of calcium carbonate added. Calcium carbonate can be directly supplied to the sedimentation zone 5 through a line 15. Since calcium carbonate does not directly participate in the reaction, it may also be added to the saponification zone 3. It can be added at any desired position from the saponification zone 3 to the sedimentation zone 5. When the amount of calcium carbonate and calcium hydroxide in the slurry consisting mainly of these components to be added to the neutralization zone through line 11 is insufficient for neutralizing hydrochloric acid present in the DH-containing solution resulting from the reaction, calcium carbonate can be added as a supplemental alkali through line 13. The zone 5 may be a thickner apparatus heretofore used to purify saline water for electrolysis.

Preferably, the amount of calcium carbonate to be added is such that the amount of calcium carbonate in the residual slurry in the zone 5 is about 95 to about 97% by weight, based on the weight of the solids in the slurry.

A slurry containing mainly magnesium hydroxide in the sedimentation zone 5 is discharged from the top of the zone 5, and conducted to the sedimentation zone 6 through line 12, where magnesium hydroxide is sedimented. It is then withdrawn from line 17, and the supernatant liquid is withdrawn from line 16 and after neutralization can be discharged as a waste. Since magnesium hydroxide withdrawn scarcely contains calcium but has a high Mg purity, it can be effectively utilized.

According to the conventional process, the residual slurry left after the separation of EP in the zone 4 is conducted to a sedimentation tank to sediment a slurry containing calcium carbonate, calcium hydroxide, and magnesium hydroxide. Since the speed of sedimentation of magnesium hydroxide is slow, the sedimentation tank requires a huge capacity. The supernatant liquid can be discarded after being directly neutralized to a pH of about 7. The slurry sedimented is treated with hydrochloric acid to a pH of about 1 in a dissolving tank equipped with stirrer in order to dissolve the magnesium hydroxide completely, and then neutralized with an alkali to a pH of about 7 before it is discarded. Thus, very great amounts of hydrochloric acid are required in order to treat all of the slurry, and the amount of the waste water to be treated also increases. However, according to the present invention, the residual slurry can be discharged by far simpler operations and apparatus, and moreover, the neutralization can be advantageously performed on an industrial scale by utilizing a part of the residual slurry. Furthermore, the amount of expensive calcium hydroxide can be markedly reduced, and epichlorohydrin can be obtained in high yields while conveniently inhibiting side reactions.

The following Examples and Comparative Examples illustrate the present invention in greater detail.

In these examples, the slaked lime used contained 96.0% by weight $Ca(OH)_2$, 2.0% by weight $CaCO_3$ and 1.0% by weight MgO, and calcium carbonate used was $CaCO_3$ having a purity of 99.0%.

EXAMPLE 1

Glycerol dichlorohydrin (DH) was continuously produced by the embodiment shown in FIG. 1. In reaction zone 1, 40 g/min. of allyl chloride and 40 g/min. of chlorine were added to 2.0 kg/min. of water, and the mixture was stirred to form an aqueous solution containing 66.0 g/min. of DH and 18.5 g/min. of hydrochloric acid and acidified with the hydrochloric acid formed. The aqueous solution obtained was fed into neutralization zone 2, and neutralized while feeding 250 ml/min. of the recycle slurry containing 1.15 g/min. of calcium hydroxide and 23.8 g/min. of calcium carbonate separated in the separating zone 5 into neutralization zone 2. The neutralized solution was conducted to saponification zone 3, and 21.0 g/min. of slaked lime and 25.3 g/min. of calcium carbonate were added to saponify the neutralized solution. The resulting liquid containing epichlorohydrin (EP) as a product was fed into separating zone 4 to separate and recover EP by azeotropic distillation in a conventional manner. The amount of EP formed at this time was 44.8 g/min.

On the other hand, the residual slurry left after the separation of EP was introduced into sedimentation zone 5 at a rate of about 2 liters/min. [25.4 g/min. of $CaCO_3$, 0.3 g/min. of $Mg(OH)_2$ and 1.22 g/min. of $Ca(OH)_2$], and a slurry containing mainly calcium carbonate and calcium hydroxide was sedimented and separated. The slurry was recycled to neutralizing zone 2 through line 11 at a rate of 250 ml/min. The waste slurry at the upper part containing mainly magnesium hydroxide was introduced into the sedimentation zone 6 where a component consisting mainly of magnesium hydroxide was sedimented and separated, and discharged out of zone 6.

The rate of recovery of calcium carbonate and calcium hydroxide at sedimentation zone 5 was 91 to 94%. The amount of waste slurry formed in sedimentation zone 6 was 1.5 to 2.0 g/min. The yield of EP and other results are shown in Table 1 (the results in other examples are also shown in Table 1).

EXAMPLE 2

Example 1 was repeated except that slaked lime for saponification was added to saponification zone 3 at a rate of 21.0 g/min., 23.8 g/min. of calcium carbonate was added to neutralization zone 2, and the slurry recovered from zone 5 was recycled to zone 2 at a rate of 15 ml/min. [0.38 g/min. of $CaCO_3$ and 1.10 g/min. of $Ca(OH)_2$]. The rate of recovery of calcium hydroxide and calcium carbonate (to be referred to simply as "recovery rate") from the sedimentation zone 5 was 87 to 91%. The amount of the waste slurry formed in the sedimentation zone 6 was 0.30 to 0.50 g/min.

EXAMPLE 3

Example 1 was repeated except that slaked lime for saponification was added to the saponification zone 3 at a rate of 21.0 g/min., and calcium carbonate was added to sedimentation zone 5 for promotion of sedimentation at a rate of 25.1 g/min. The recovery rate was 92 to 96%, and the amount of the waste slurry formed in sedimentation zone 6 was 1.5 to 2.0 g/min.

EXAMPLE 4

Example 1 was repeated except that slaked lime for saponification was added to saponification zone 3 at a rate of 42.0 g/min. A slurry containing 18.4 g/min. of calcium hydroxide and 0.72 g of calcium carbonate was recycled to neutralization zone 2. The recovery rate was 85 to 88%.

EXAMPLE 5

Example 1 was repeated except that 320 g/min. of slaked lime and 20.7 g/min. of a 48% by weight solution of sodium hydroxide were added to saponification zone 3. A slurry from zone 5 containing 18.5 g/min. of calcium hydroxide and 0.56 g/min. of calcium carbonate was recycled to neutralization zone 2. The recovery rate was 85 to 90%.

EXAMPLE 6

Example 1 was repeated except that 36.5 g/min. of slaked lime and 10.3 g/min. of a 48% solution of sodium carbonate were added to saponification zone 3. A slurry from zone 5 containing 18.4 g/min. of calcium hydroxide and 0.65 g/min. of calcium carbonate was recycled to neutralization zone 2. The recovery rate was 85 to 90%.

EXAMPLE 7

Example 1 was repeated except that 10.7 g/min. of slaked lime and 21.5 g/min. of a 48% by weight solution of sodium hydroxide were added to saponification zone 3, and 25.6 g/min. of calcium carbonate was added in sedimentation zone 5. A slurry from zone 5 containing 0.91 g/min. of calcium hydroxide and 24.3 g/min. of calcium carbonate was recycled to neutralization zone 2. The recovery rate was 92 to 96%.

EXAMPLE 8

A 48% by weight solution of sodium hydroxide was added to neutralization zone 2 at a rate of 39.0 g/min., and simultaneously, a slurry from sedimentation zone 5 containing 1.10 g/min. of calcium hydroxide and 0.37 g/min. of calcium carbonate was recycled to neutralization zone 2. Furthermore, 21.0 g/min. of slaked line was added to saponification zone 3. Otherwise, the same procedure as in Example 1 was repeated. The recovery rate in sedimentation zone 5 was 85 to 90%. The amount of the waste slurry formed in sedimentation zone 6 was 0.30 to 0.50 g/min.

COMPARATIVE EXAMPLE 1

The recycling method was not employed, but the aqueous layer from separating zone 4 was directly withdrawn outside the zone. Furthermore, no neutralization zone was provided but only slaked lime as an alkali required in the entire process was added to saponification zone 3 at a rate of 42.0 g/min. Otherwise, the procedure was the same as in Example 1. The amount of the waste slurry formed was 5.5 to 4.5 g/min.

COMPARATIVE EXAMPLE 2

Example 1 was repeated except that 1.20 g/min. of magnesium hydroxide was added to the saponification zone 3.

Table 1

| Example (Ex.) and Comparative Example (CE.) | Yield (%) of epichlorohydrin | Unit cost of line | Unit cost of calcium carbonate | Unit cost of sodium hydroxide (calculated on 100%) | COD in the waste slurry (ppm) |
|---|---|---|---|---|---|
| Ex. 1 | 92.2–93.1 | 460–490 | 560–590 | — | 720–750 |
| Ex. 2 | 92.0–93.2 | 460–490 | 510–530 | — | 700–740 |
| Ex. 3 | 91.8–93.0 | 460–490 | 550–580 | — | 720–750 |
| Ex. 4 | 85.0–87.2 | 950–1020 | — | — | 830–900 |
| Ex. 5 | 89.0–91.0 | 700–740 | — | 220–240 | 870–910 |
| Ex. 6 | 88.1–91.0 | 800–860 | — | 100–120 | 850–900 |
| Ex. 7 | 93.0–93.8 | 230–260 | 560–590 | 220–240 | 700–750 |
| Ex. 8 | 81.0–83.0 | 520–550 | — | 470–490 | 930–960 |
| CE. 1 | 79.1–80.0 | 1030–1100 | — | — | 1300–1350 |
| CE. 2 | 71.1–72.8 | 590–630 | 720–760 | — | 1490–1580 |

1) The yield of epichlorohydrin is based on allyl chloride.
2) The unit cost is in terms of the amount in grams of each compound per kilogram of epichlorohydrin.

What we claim is:

1. A process for continuously producing epichlorohydrin which comprises reacting chlorine and allyl chloride in an aqueous medium to produce an hydrochloric acid-acidified solution containing glycerol dichlorohydrin, neutralizing the resulting acidified solution with an alkali selected from the group consisting of calcium carbonate, calcium hydroxide and a mixture thereof in a neutralization zone, saponifying the resulting neutralized solution in a saponification zone, separate from the neutralization zone, by adding calcium hydroxide to form a solution containing epichlorohydrin, separating epichlorohydrin from the saponified solution to form a residual slurry, separating said residual slurry in a slurry separating zone into a first slurry containing mainly calcium carbonate and calcium hydroxide, and a second slurry containing magnesium hydroxide, recycling the first slurry containing mainly calcium carbonate and calcium hydroxide to the neutralization zone, and, withdrawing the second slurry containing mainly magnesium hydroxide.

2. The process of claim 1 wherein the first slurry containing mainly calcium carbonate and calcium hydroxide is separated from the residual slurry in the presence of calcium carbonate added.

3. The process of claim 2 wherein calcium carbonate is added at any desired position from the saponification zone to the slurry-separating zone.

4. The process of claim 1 wherein the second slurry consisting mainly of magnesium hydroxide is subjected to a sedimentation treatment to sediment and separate the magnesium hydroxide.

* * * * *